(12) United States Patent
Krimsky

(10) Patent No.: US 10,881,780 B2
(45) Date of Patent: Jan. 5, 2021

(54) VASCULAR ISOLATION SYSTEMS AND METHODS

(71) Applicant: COVIDIEN LP, Mansfield, MA (US)

(72) Inventor: William S. Krimsky, Forest Hill, MD (US)

(73) Assignee: COVIDIEN LP, Mansfield, MA (US)

( * ) Notice: Subject to any disclaimer, the term of this patent is extended or adjusted under 35 U.S.C. 154(b) by 36 days.

(21) Appl. No.: 16/451,175

(22) Filed: Jun. 25, 2019

(65) Prior Publication Data

US 2019/0307945 A1 Oct. 10, 2019

Related U.S. Application Data

(63) Continuation of application No. 15/144,888, filed on May 3, 2016, now Pat. No. 10,328,195.

(51) Int. Cl.
*A61M 1/36* (2006.01)
*A61B 6/00* (2006.01)
(Continued)

(52) U.S. Cl.
CPC ......... *A61M 1/3659* (2014.02); *A61B 1/2676* (2013.01); *A61B 6/461* (2013.01); *A61B 6/507* (2013.01); *A61B 8/06* (2013.01); *A61B 8/085* (2013.01); *A61B 8/0841* (2013.01); *A61B 8/12* (2013.01); *A61B 8/461* (2013.01); *A61B 8/488* (2013.01); *A61B 17/122* (2013.01); *A61B 17/1204* (2013.01); *A61B 17/12109* (2013.01); *A61B 34/20* (2016.02); *A61B 34/25* (2016.02); *A61B 90/37* (2016.02); *G06T 19/00* (2013.01); *A61B 17/1285* (2013.01);
(Continued)

(58) Field of Classification Search
CPC ....... A61B 18/1492; A61B 34/20; A61B 8/12; A61B 17/12104; A61F 2/04; A61M 25/1011
See application file for complete search history.

(56) References Cited

U.S. PATENT DOCUMENTS 8,409,166 B2  4/2013  Wiener et al.
8,998,893 B2  4/2015  Avitall
(Continued)

FOREIGN PATENT DOCUMENTS

WO  0010456 A1  3/2000
WO  0167035 A1  9/2001
(Continued)

OTHER PUBLICATIONS

European Search Report dated Oct. 5, 2017 issued in corresponding European Application No. 17169264.3.
(Continued)

*Primary Examiner* — Manuel A Mendez

(57) ABSTRACT

A system and method enabling the receipt of image data of a patient, identification of one or more locations within the image data depicting symptoms of lung disease, analyzing airways and vasculature proximate the identified locations, planning a pathway to the one or more locations, navigating an extended working channel to one of the locations, identifying the direction of blood flow within vasculature serving the location, positioning a catheter proximate the location, and temporarily isolating a portion of the identified vasculature serving the location depicting symptoms of lung disease.

20 Claims, 4 Drawing Sheets

(51) Int. Cl.
*A61B 1/267* (2006.01)
*A61B 8/08* (2006.01)
*A61B 8/00* (2006.01)
*G06T 19/00* (2011.01)
*A61B 34/20* (2016.01)
*A61B 34/00* (2016.01)
*A61B 90/00* (2016.01)
*A61B 8/06* (2006.01)
*A61B 8/12* (2006.01)
*A61B 17/12* (2006.01)
*A61B 17/122* (2006.01)
*A61B 17/128* (2006.01)
*A61B 17/00* (2006.01)
*A61B 18/00* (2006.01)
*A61B 34/10* (2016.01)

(52) U.S. Cl.
CPC .................. *A61B 17/12131* (2013.01); *A61B 2017/00809* (2013.01); *A61B 2018/00541* (2013.01); *A61B 2018/00982* (2013.01); *A61B 2034/107* (2016.02); *A61B 2090/3784* (2016.02); *A61M 2205/502* (2013.01); *A61M 2210/1035* (2013.01); *A61M 2210/1039* (2013.01); *G06T 2207/30061* (2013.01)

(56) References Cited

U.S. PATENT DOCUMENTS

| | | |
|---|---|---|
| 9,149,320 B2 | 10/2015 | Kuck et al. |
| 9,463,304 B2 | 10/2016 | Agah et al. |
| 2009/0118612 A1 | 5/2009 | Grunwald et al. |
| 2009/0284255 A1 | 11/2009 | Zur |
| 2011/0085720 A1 | 4/2011 | Barak et al. |
| 2013/0223702 A1 | 8/2013 | Holsing et al. |
| 2014/0163371 A1 | 6/2014 | Matsui et al. |
| 2014/0336690 A1 | 11/2014 | Zhadkevich |
| 2015/0018762 A1 | 1/2015 | Fierens et al. |
| 2015/0265257 A1 | 9/2015 | Costello et al. |
| 2016/0000302 A1 | 1/2016 | Brown et al. |
| 2016/0038248 A1 | 2/2016 | Bharadwaj et al. |
| 2017/0202543 A1 | 7/2017 | Herdina et al. |

FOREIGN PATENT DOCUMENTS

| | | |
|---|---|---|
| WO | 2013078235 A1 | 5/2013 |
| WO | 2014106253 A1 | 7/2014 |

OTHER PUBLICATIONS

Canadian Second Office Action dated Nov. 23, 2018 issued in corresponding CA Appln. No. 2,965,931.

European Examination Report dated Feb. 4, 2019 issued in corresponding EP Appln. No. 17169264.3.

Canadian Office Action dated Mar. 5, 2018 issued in corresponding Canadian Application No. 2,965,931.

Australian Examination Report dated Nov. 22, 2017 issued in corresponding Australian Appln. No. 2017202736.

Canadian Office Action dated Aug. 27, 2019 issued in corresponding CA Appln. No. 2,965,931.

VASCULAR ISOLATION SYSTEMS AND METHODS

CROSS-REFERENCE TO RELATED APPLICATIONS

This application is a continuation of U.S. patent application Ser. No. 15/144,888, filed on May 3, 2016, the entire contents of which are incorporated herein by reference.

INTRODUCTION

The present disclosure relates to surgical systems, and more particularly, to systems and methods of vascular isolation.

BACKGROUND

Tens of millions of people suffer from lung disease, such as emphysema, chronic obstructive pulmonary disease ("COPD"), asthma, interstitial lung disease, cancer, or myriad other afflictions affecting the lungs. Diseases such as emphysema result in poor airflow due to a breakdown of lung tissues. In patients suffering from emphysema the alveoli are no longer elastic and can become enlarged due to walls between the alveoli breaking down. As a result, the alveoli lose their shape and become floppy. This damage from emphysema leads to fewer and larger air sacs instead of many tiny ones. These large alveoli may be called bullae. One result of this breakdown of the alveoli is that the volume of gas exchange that can occur is reduced as the surface area of these fewer enlarged alveoli is less than the many smaller alveoli. Additionally, the weakened floppy alveoli easily expand during an inhalation. Because of the weakened condition, the air having entered the weakened alveoli cannot be forced out of the lungs during exhalation. Deoxygenated air is trapped inside of the damaged floppy alveoli. This trapped air, however, keeps the alveoli expanded and thus takes up precious volume in the chest cavity. By taking up volume in the chest cavity, the volume available for inhalation of oxygenated air decreases, effectively preventing the patient from ever satisfying their need for oxygen. A patient suffering from emphysema will typically appear thin, and take very rapid low volume breaths. As can be imagined, the problem of easy filling and poor emptying of the lung leads to progressive hyperexpansion of the lungs, increased residual volume, reduced capacity, inefficient breathing mechanics, and in general, a continually worsening patient condition as they struggle to inspire sufficient volume of air. The classic description is that the patient will appear as a "pink puffer," because the patient will be constantly working in an effort to inspire any oxygen into their overinflated lung tissues.

Chronic bronchitis is the result of excessive mucus build-up in the bronchioles. Often this mucus production is part of an inflammatory response caused by injury to the airways from smoking and other inhaled antagonists. The mucus can be so excessive that it overcomes the ability of the cilia within the lungs to sweep the mucus out and allow it to be expelled. Further, the mucus limits the size of the airways through which air must travel in the lungs, thus limiting the volume of air that can be inhaled. The combined effect causes a sufferer to persistently cough in a futile attempt to clear the mucus. This mucus can be so excessive that as it is drawn further and further distal in the lungs (e.g., to the alveoli which might not themselves be inflamed) the mucus limits the gas exchange as it coats the alveoli walls. The mucus reaching the alveoli further exacerbate the challenges of gas transfer experienced by smokers, where tar and other contaminates may already be covering the lining of the alveoli creating a barrier for gas exchange. Further, the mucus and other contaminants are a breeding ground for bacterial growth, promoting further infection and even greater bronchitis symptoms. The classic description of someone suffering from chronic bronchitis is a "blue bloater." The color refers to the lack of oxygen successfully transferring form the alveoli to the blood stream and $CO_2$ being expelled from the blood stream through the alveoli to the atmosphere. These patients often appear bloated due to obesity as well as water retention as a result of their compromised pulmonary and circulatory functions. As will be appreciated, many if not most patients will suffer from both emphysema issues and chronic bronchitis issues.

Fully functioning alveoli can often adapt and at least partially compensate for the reduction in total lung capacity caused by emphysema COPD. Indeed, this is one reason for the highly invasive Lung Volume Reduction Surgery (LVRS), where wedges of damaged lung are removed to allow the remaining tissue to function better. In part, this improved performance is enabled by the increase in space afforded the remaining alveoli to expand when the damaged portions of the lung are removed. By reducing the lung size, the remaining lung and surrounding muscles (intercostal and diaphragm) are able to work more efficiently. This makes breathing easier and helps patients achieve greater quality of life.

Aside from the highly invasive LVRS, the standard of care for lung diseases, such as asthma and COPD including emphysema and chronic bronchitis has been focused largely on pharmaceutical treatment modalities. For example, ADVAIR®, a bronchodilator is currently marketed by GlaxoSmithKline plc. for the treatment of COPD. Alternatively, it has been reported for decades that lung denervation via invasive means (e.g., surgery) may provide therapeutic benefit for asthma or emphysema. Again such surgical treatment is invasive and results in the disablement of whole or parts of functions of the nerve that affects contraction of the damaged alveoli.

While these treatment options are effective to a point, the primary prescription for patients suffering from COPD is simply the administration of oxygen. Oxygen can alleviate some symptoms but does nothing to treat the underlying diseases.

SUMMARY

The present disclosure is directed to a system including a memory storing one or more images of a patient and one or more software application, and a display presenting the one or more images of a patient. The display also presents a user interface in combination with the displayed one or more images of a patient enabling the identification of one or more image locations depicting symptoms of lung disease and the identification of vascular structures within a patient's lungs serving the identified image locations. The system further includes an extended working channel navigable to one or more actual locations within a patient corresponding to the one or more image locations, a processor executing one of the one or more software applications to identify the direction of blood flow within the identified vascular structures of a patient's lungs, and a catheter, extendible through the extended working channel to temporarily isolate a portion of the identified vascular structures within a patient serving the one or more image locations depicting symptoms of lung disease.

In a further aspect, the system may include an endobronchial ultrasound scope capable of using Doppler analysis to identify the direction of blood flow within the identified vascular structures of a patient's lungs.

In another aspect, the catheter may include at least one cannula deployable therefrom configured to cannulate the identified vascular structure of a patient's lungs.

In yet another aspect, the catheter may include at least one clamp deployable therefrom configured to clamp the identified vascular structure of a patient's lungs. In another aspect, the system may include an endoscopic clip applier extendible through the catheter.

In a further aspect, the system may include an endoscopic vessel sealer extendible through the catheter.

In yet another aspect, the identified vascular structure is selected from the group consisting of the pulmonary circulatory system and the bronchial circulatory system.

In another aspect, the system may further include a tool capable of introducing drugs within the isolated portion of the identified vascular structure.

A further aspect of the present disclosure is directed to a method enabling the receipt of an image of a patient's lungs, identification of an area of interest on the image, navigating a first tool to the area of interest, the first tool capable of determining the direction of blood flow within the vascular structure within a patient's lungs serving the area of interest, identification of the direction of flow within the vascular structure within a patient's lungs serving the area of interest, and temporarily obstructing the flow of blood within the vascular structure of a patient's lungs serving the area of interest, thereby isolating a portion of the circulatory system serving the lungs.

In another aspect, navigating a first tool to the area of interest may include navigating an endobronchial ultrasound scope to the area of interest using ultrasound images obtained by the endobronchial ultrasound scope.

In a further aspect, identifying the direction of flow within the vascular structure within a patient's lungs serving the area of interest may include using doppler flow capabilities of the endobronchial ultrasound scope to identify the direction of blood flow within the vascular structure of a patient's lungs serving the area of interest.

In yet another aspect, the method may include navigating a second tool to the area of interest and temporarily obstructing flow of blood within the vascular structure serving the area of interest using the second tool to cannulate the vascular structure serving the area of interest.

In a further aspect, the method may include performing an extracorporeal procedure on the vascular structure serving the area of interest.

In another aspect, performing an extracorporeal procedure may include introducing a drug to treat the isolated portion of the circulatory system serving the lungs.

In yet another aspect, temporarily obstructing flow of blood within the vascular structure serving the area of interest may include temporarily obstructing flow of blood within the pulmonary circulatory system serving the area of interest.

In another aspect, temporarily obstructing flow of blood within the vascular structure serving the area of interest may include temporarily obstructing flow of blood within the bronchial circulatory system serving the area of interest.

In a further aspect, the method may include directly administering drugs to the isolated portion of the circulatory system serving the lungs.

A further aspect of the present disclosure is directed to a method of performing a surgical procedure including acquiring an image of a patient's lungs, identifying an area of interest on the acquired image, identifying a similar patient from a database stored within a memory coupled to a computer, the memory capable of being executed by a processor, predicting the clinical effects of isolating a portion of the circulatory system within a patient's lungs serving the area of interest, and isolating the portion of the circulatory system within a patient's lungs serving the area of interest.

In a further aspect, predicting the clinical effects of isolating a portion of the circulatory system may include predicting a dose of drugs to administer to the isolated portion of the circulatory system within a patient's lungs serving the area of interest.

In another aspect, the method may include administering a predicted dose of drugs to the isolated portion of the circulatory system within a patient's lungs serving the area of interest.

BRIEF DESCRIPTION OF THE DRAWINGS

Various aspects and features of the present disclosure are described hereinbelow with references to the drawings, wherein.

DETAILED DESCRIPTION

Figure 1:
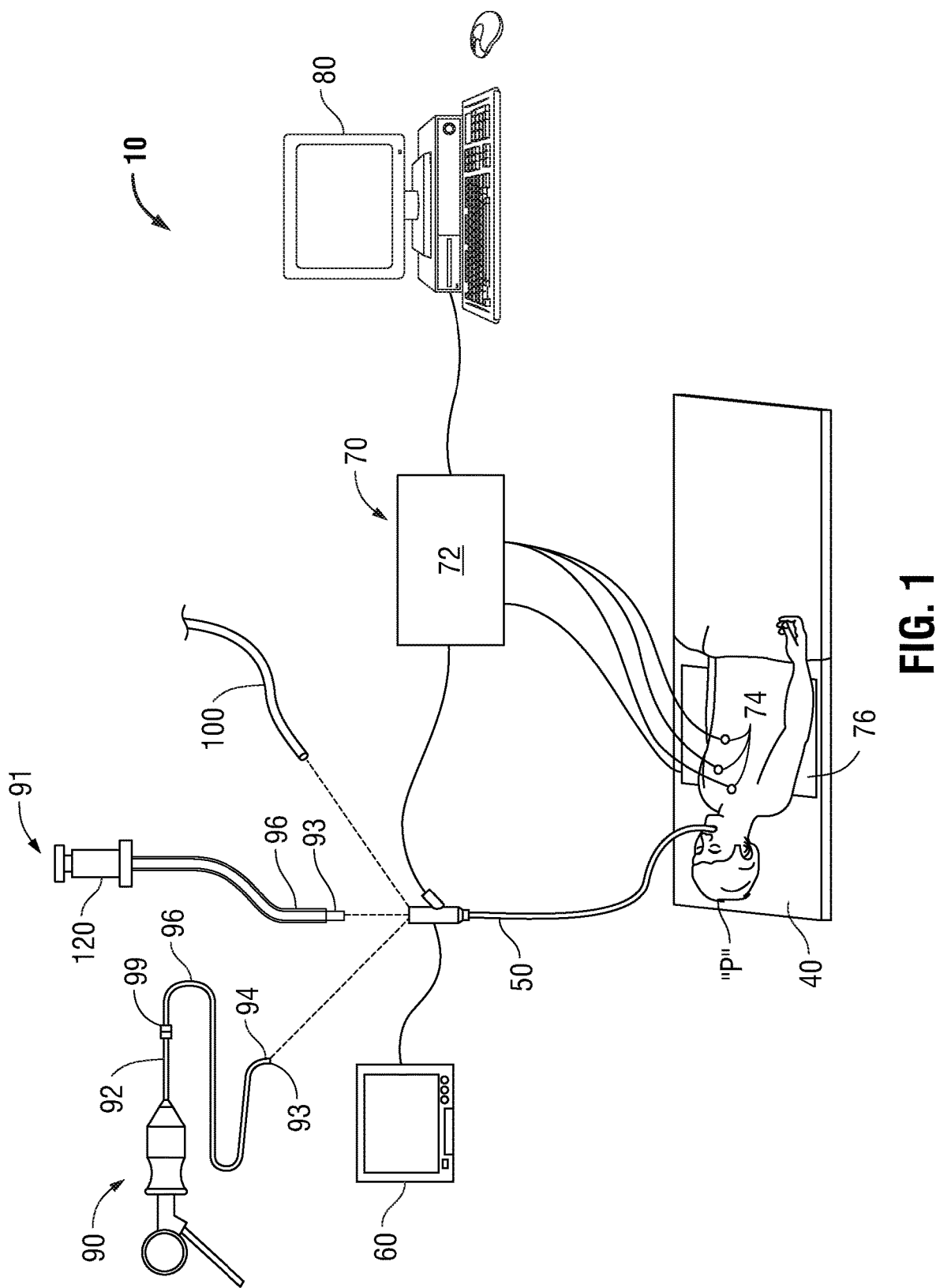
FIG. 1 is a perspective view of a system provided in accordance with the present disclosure capable of navigating a tool to an area of interest and isolating a portion of the circulatory system within the lungs.

The present disclosure is directed to systems and methods of identification of vasculature supporting identified diseased portions of the lungs or areas of the lungs whereby delivery of therapeutics to the vasculature, or a portion of the vasculature, may enhance the efficacy of therapeutics, such as gene vectors or the like, delivered thereto. More particularly, the present disclosure is directed to methods and systems of reversibly limiting blood flow to certain diseased portions of the lungs to assess the efficacy of a proposed treatment, in some instances, through the use of an Electromagnetic Navigation (EMN) System or Electromagnetic Navigation Bronchoscopy (ENB™). One effect of isolating portions of the lungs by restricting blood flow is that blood flow is re-directed to other areas of the lungs. This can result in an effective increase in ventilation and perfusion matching (V/Q) as an increased volume of blood is directed to areas where gas exchange can be improved rather than continuing to deliver blood to the more diseased portion of the lungs. This also may result in deleterious effects such as substantive elevations in pulmonary vascular pressure among others but as, this can be done reversibly, if those are encountered, they can be reversed. Regardless, by understanding these outcomes prior to making the change permanent, such as with surgery and lung resection will allow for a more specific and through assessment of the effect. These effects can be readily measured through the use of blood gas analyzers and other diagnostic tools as will be described in detail below. Over time, a database may be built using the data obtained during each reversible isolation procedure. This database may be indexed such that clinicians may review data obtained from similar patients to better predict the outcome of the procedure as well as the effects of the reversible procedure on the pulmonary circulation, the development of elevated pulmonary pressures, etc.

Isolation and identification of vascular structures within the lungs are critical aspects of many procedures. Specifically, identification of vascular pedicles (i.e., the tissues containing arteries and veins) within the lungs establishes the boundaries for lung resection and locations for the placement of clamps that isolate the affected portion of the lung. However, identification of vascular structures such as inflow and outflow tracts, and arteries, and veins within the lung permits a clinician to temporarily isolate an affected portion of the lungs, either by isolating a portion of the pulmonary circulatory system within the lung, isolating a portion of the bronchial circulatory system within the lung, or both, such that treatment of the affected portion of the lung is isolated thereto. Indeed, such isolation would prevent systemic exposure to high concentrations of drugs, or in the instance where resection is necessary, a large heat sink (in the form of blood within the vascular structure) is removed, thereby enabling a clinician to better focus ablation to the affected portion and reduce the amount of damage to surrounding tissue. The systems and methods of the present disclosure enable a clinician to accurately identify the vascular structures serving the diseased portions of the lung in order to provide direct treatment thereto. Detailed embodiments of such systems and methods are described below. However, these detailed embodiments are merely examples of the present disclosure, which may be embodied in various forms. As will be appreciated, the following systems and methods may also serve to identify aberrant vascular structures in these areas. In this manner the surgeon may be alerted such that the operative resection may be altered to account for this aberrancy pre-operatively. In a similar manner, it is contemplated that the proceduralist may be alerted for the same reason.

Although the systems and methods detailed herein are generally described with respect to the lungs, it is contemplated that the following systems and methods may be applied to any organ having dual blood supplies (e.g., the liver). Similarly to that described below with respect to the lungs, it is envisioned that any organ having dual blood supplies may be treated by means of either an endoscopic or percutaneous approach.

With reference to FIGS. 1-5, a method of temporarily isolating portions of the vascular structures within the lungs using an endoscopic approach is described. Initially, patient characteristics are recorded in a memory coupled to a computer 80 (FIG. 1). The memory may include any non-transitory computer-readable storage media for storing data and/or software that is executable by a processor (not shown), e.g., solid-state, volatile, non-volatile, removable, and non-removable. Patient characteristics may include, but are not limited to, age, sex, race, lung volume, disease type, respiration rate, observed overinflation, smoking history, oxygen saturation, or the like. Next, the patient is imaged using any suitable imaging device (not shown), such as MRI, ultrasound, CT scan, Positron Emission Tomography (PET), or the like, and the images are stored within the memory coupled to computer 80 (FIG. 1). As can be appreciated, the image obtained by the imaging device may be correlated or indexed to patient data to enable a clinician to look-up similarly situated patients. In this manner, the clinician may better predict the clinical consequences of isolating the particular portion of the vascular structure of the patient's lungs, as will be described in further detail hereinbelow.

Following imaging, a software application may be initiated to enable review of the image data. One example of such an application are the ILOGIC® planning and navigation suites currently marketed by Medtronic. An area of interest (AOI) is identified in the images and its location determined within the lungs of the patient. Several methods of identifying an area of interest are contemplated. In one non-limiting embodiment, where the patient is not suffering from easily identified lesions or cancers of the lungs, the results of images generated from a CT scan can be analyzed to identify areas of hypodensity. Hypodense portions of the lungs are areas where the density of the tissue is less than the surrounding tissue. This may be particularly useful for patients suffering from emphysema as the expanded floppy alveoli or bullae will provide images that have areas which may be substantially black, indicating that they are largely air with little to no tissue separating these enlarged alveoli. Because of this hypodensity, image analysis using 3D image processing is particularly useful as identification of these areas where the densities of the images (measured in Hounsfield units of HU) is below a certain threshold (e.g., −950 HU) approximately the same as air. This 3D rendering is relatively straightforward and even coarse thresholding can be employed to distinguish the enlarged alveoli from tissue and identify their locations in the CT images. These coarse threshold values can then be rendered as a 3D model of the affected areas of the lungs.

Separately, the CT image data may be processed to identify all of the vascular structure within the lungs. Again, a 3D model of this vasculature can be generated. Techniques for generating 3D volumetric rendering are described in U.S. patent application Ser. No. 14/821,950 to Bharadwaj et al., entitled "Treatment Procedure Planning System and Method," filed Aug. 10, 2015, the entire contents of which are hereby incorporated by reference herein. As will be appreciated, the generation of a 3D map of the vasculature may be more challenging than of the hypodense areas. As an alternative to generation of a 3D map of the vasculature from the CT scan, an angiogram or a CT angiogram may be separately undertaken. In an angiogram, radiographic fluids are injected into the patient and used to identify the precise location of the vasculature in the images. The identification of the vasculature is made much easier by the addition of these radiographic fluids as they resolve themselves much more clearly in the X-ray and CT images. Where a CT angiogram is undertaken, the images of the vasculature can be registered to the images mapping the hypodensities in the lungs to create a composite image set revealing the interaction of the vasculature with the hypodense areas.

In an alternative embodiment, PET imaging may be utilized to identify areas of low metabolic activity within the lungs. As can be appreciated, a device capable of performing a combined PET/CT imaging technique may be utilized, which has proven to be quite accurate. These areas of very little metabolic activity should closely correspond to areas of overinflated alveoli. There is very little metabolic activity in these areas because they are mostly comprised of air. In this way, a PET image set can be utilized to identify the hypodense areas to which navigation and treatment should be directed. After careful analysis, using one of the above described techniques, the location of the area of interest may be identified and its location stored within the memory coupled to computer 80 (FIG. 1).

Additionally, the following systems and methods employ the use of Endobronchial Ultrasound (EBUS) and EMN, although it is contemplated that the systems and method described hereinbelow utilize may only an EBUS scope for navigation through the luminal network of the lungs and identification of vascular structures. An EBUS scope is an endoscopic tool including an ultrasound transceiver capable of emitting and receiving ultrasound signals and displaying a resulting image on a suitable monitor. EBUS devices generate Doppler images of the layers of the bronchial wall and structures adjacent to the airways. Certain EBUS devices (e.g., CP-EBUS) employ the use of color Doppler visualization which enables a clinician to identify blood flow, and thus, identify the particular type of vascular structures adjacent the bronchial walls. Examples of such EBUS devices are manufactured by Olympus Corporation, Pentax Medical, and Fijifilm. As can be appreciated, any device known in the art and capable of identifying vascular structures and the direction of blood flow may be utilized.

Figure 2A:
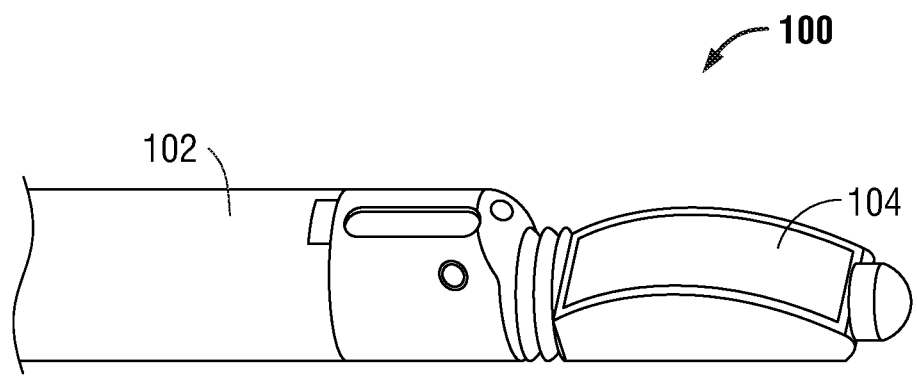
FIG. 2A is a partial perspective view showing the distal portion of an Endobronchial Ultrasound (EBUS) scope configured for use with the system of FIG. 1.
Figure 2B:
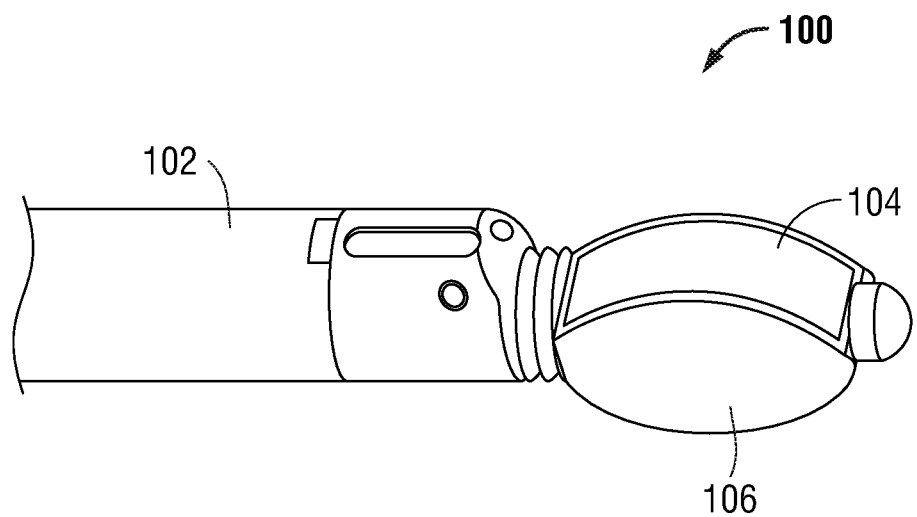
FIG. 2B is a partial perspective view showing the distal portion of the EBUS scope of FIG. 2A, shown with a distal balloon inflated.

An example of a CP-EBUS scope suitable for use with the present disclosure is illustrated in FIGS. 2A and 2B and generally identified by reference numeral 100. EBUS scope 100 includes a flexible elongate member 102 configured to be extendable within a working channel of a bronchoscope or extended working channel (EWC), such as bronchoscope 50 and EWC 96 of the present disclosure, as will be described in further detail hereinbelow. A distal end of EBUS scope 100 includes an ultrasonic transducer 104 capable of scanning adjacent tissue and displaying the resulting images on a monitor (such as monitoring equipment 60, detailed below). In certain instances, EBUS scope 100 includes an inflatable balloon 106 disposed on a distal end of elongate member 102 (FIG. 2A). Ultrasonic transducer 104 is disposed within inflatable balloon 106 and submerged in a saline solution such that ultrasonic transducer 104 is not required to be in direct contact with tissue in order to obtain ultrasound images.

While it is certainly possible to navigate the luminal network of the lungs relying solely on ultrasound, the lack of directed feedback from an optical or ultrasound system alone can sometimes compromise location specificity, leading to mislabeling or mistreating of certain areas. To alleviate these issues, EBUS scope 100 may be utilized in conjunction with EMN to more accurately navigate the luminal network of the lungs and reach an area of interest. In certain instances, a clinician may employ catheters having a sensor disposed therein that is electromagnetically sensitive such that the progress of the catheter within the luminal network may be monitored. Examples of such catheters are marketed and sold by Medtronic as Edge™ and superDimension™ navigation catheters, which may be utilized with the superDimension™ Navigation system employing LungGPS™ technology. A detailed description of a planning and navigation system suitable for use with EBUS scopes is described in detail hereinbelow. As can be appreciated, the use of an EBUS scope may be utilized in conjunction with the CT angiogram procedure detailed above, thereby increasing the accuracy of the identification of the vascular structure.

After imaging and identifying an area of interest within the lungs of the patient, the clinician utilizes the software to determine a pathway through the luminal network of the lungs to the identified area of interest. Thereafter, the clinician enters the navigation phase. A bronchoscope 50 (FIG. 1) is inserted within the patient and navigated through the patient's airways and adjacent the area of interest using a tracking system 70 (FIG. 1). However, if bronchoscope 50 is unable to be navigated to the area of interest due to the size of bronchoscope 50 prohibiting further insertion, a locatable guide (LG) 92 and EWC 96 (FIG. 1) may be advanced within a working channel of bronchoscope 50 and independently navigated to the area of interest via tracking system 70. As noted above, it is contemplated that EBUS scope 100 may be utilized to navigate to the area of interest utilizing ultrasound or an electromagnetic sensor 108 disposed on a distal end thereof capable of being utilized with tracking system 70, as will be detailed hereinbelow. In this manner, EBUS scope 100 is utilized in lieu of LG 92.

Figure 3:
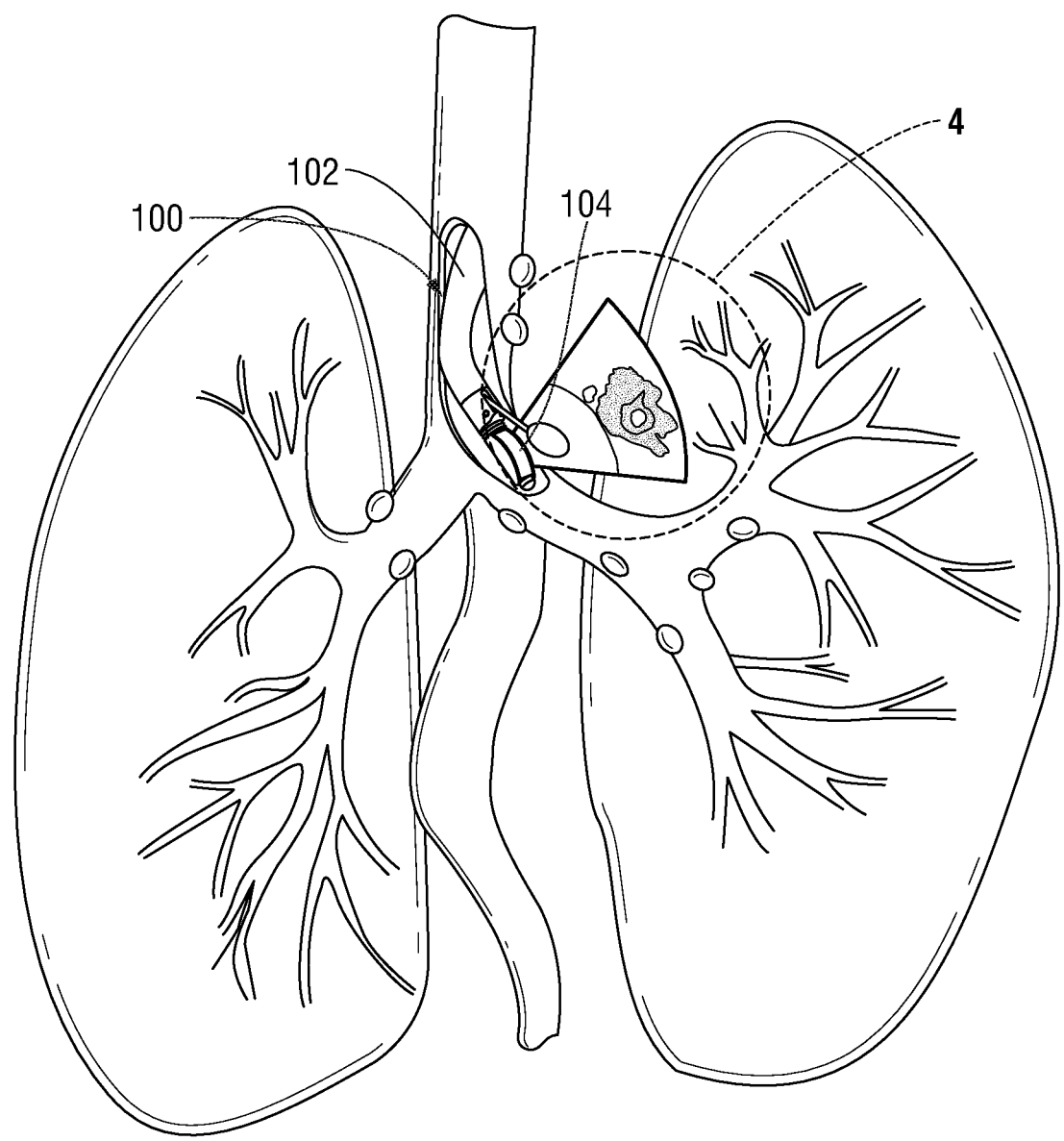
FIG. 3 is a three dimensional representation of a patient's pulmonary system illustrating the EBUS scope of FIG. 2 advanced within the airways of a patient.

Once the EWC 96 is placed proximate the area of interest, the LG 92 may be removed from EWC 96 and EBUS scope 100 may be inserted within EWC 96 and navigated to the area of interest (FIG. 3). Alternatively, both LG 92 and EWC 96 may be withdrawn from the working channel of bronchoscope 50 and EBUS scope 100 may be advanced within the working channel of bronchoscope 50 and navigated to the area of interest by means of ultrasound imaging and/or sensor 108. In another embodiment, EBUS scope 100 may be advanced within the airways a patient without the use of bronchoscope 50 and navigated to the area of interest by means of ultrasound imaging and/or sensor 108.

Figure 4:
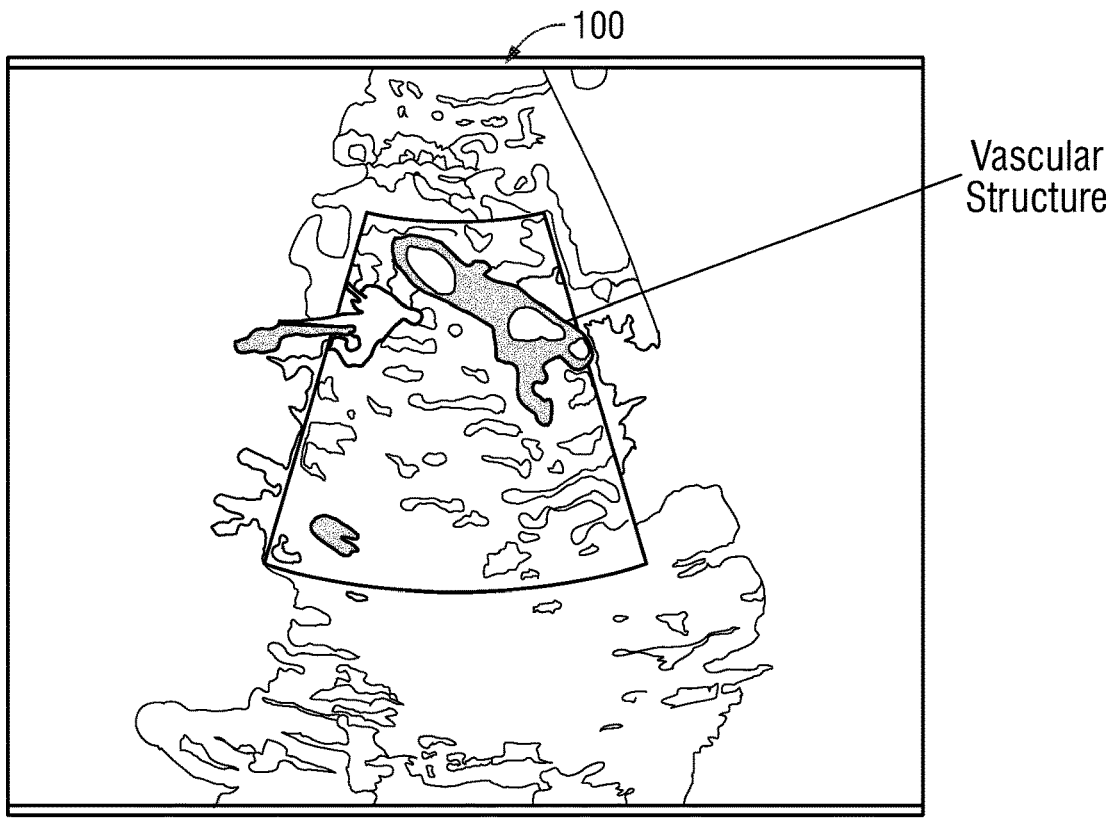
FIG. 4 is a graphical representation of an ultrasound image obtained by the EBUS scope of FIG. 2.

Utilizing EBUS scope 100, a method of isolating a portion of a patient's pulmonary and/or bronchial circulatory system is possible. With reference to FIG. 4, the EBUS scope 100 transmits ultrasound images to the monitoring equipment 60 as it is being advanced within the airways of the patient in proximity to the area of interest. In this manner, using the ultrasound images, the clinician monitors the structure of the patent's lungs outside of the airways. Once the vascular structures (i.e., vascular pedicle or the like) adjacent the area of interest have been identified, the clinician may use Doppler shift analysis to determine the direction of blood flow within the vascular structure (FIG. 4). Identification of the direction of flow, in combination with the clinician's understanding of physiology and the location of the EBUS scope 100 should enable a clinician to determine the nature of the vascular structure. As can be appreciated, utilizing the above described EMN system in conjunction with EBUS scope 100 (i.e., position of EBUS scope 100 within the CT volume, ultrasound images, and Doppler shift analysis), a clinician can more easily identify the vascular structure, even in instance where the vasculature structures are disposed in close relationship to one another, thereby reducing the likelihood of mislabeling or misidentifying structure within or adjacent the lungs.

Once identified, a clinician can seek to block flow to or from that particular vascular structure. In this manner, the portion of the pulmonary and/or bronchial circulatory system serving the area of interest within the patient's lungs may be isolated.

In each of the below procedures isolating pulmonary circulation, although pulmonary circulation is blocked, the cellular structure of the lungs is still kept viable by bronchial circulation. Accordingly, blood flow for the purposes of gas exchange (pulmonary circulation) is inhibited without having any effect upon bronchial circulation. As a result, the blood flow which would otherwise be directed to the other portions of the lungs is redirected to other areas with attendant effects. The lungs have the unique ability to greatly expand their volumetric blood flow Q without substantial increases in pulmonary blood pressure. In some instances this may be a four-fold volumetric increase without a substantial increase in pressure within the lungs (e.g., when running very hard). As a result, the redirecting of blood from ineffective portions of the lungs to effective portions of the lungs results in greater gas transfer at a constant volumetric flow, without an increases blood pressure. In embodiments, pulmonary blood pressure may be tested transiently to assess if there were any substantive increases in pulmonary blood pressure as a result of redirecting blood to other and potentially more effective portions of the lungs. Additionally, this capability provides clinicians with greater abilities to treat lung disease while minimizing damage to surrounding lung tissue. In this manner, the treatment chosen by the clinician can be more focused, and with a greater possibility of treating only the diseased portion of the lung or the diseased portion of the vessels.

Figure 5:
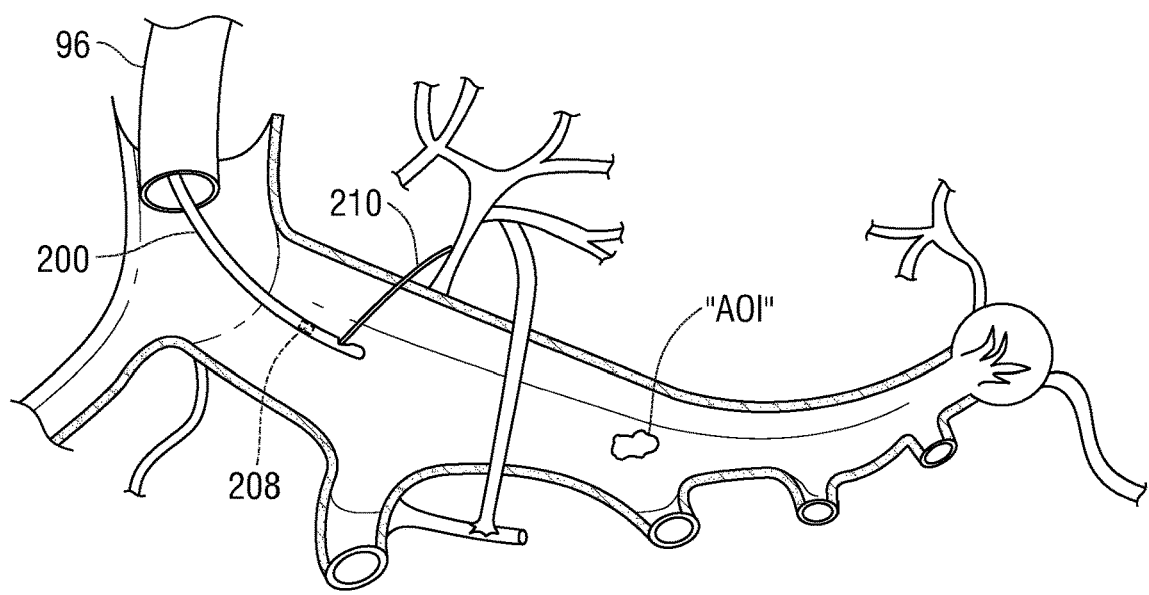
FIG. 5 is a cross-sectional view of a portion of a patient's lungs including an area of interest (AOI), shown with a tool capable of cannulating a vascular structure.

In one embodiment, after the clinician has identified the inflow and outflow tracts of the portion of the pulmonary circulatory system (using Doppler shift analysis, or other techniques to accomplish the same), the clinician can identify the vasculature serving a particular portion of the lung adjacent the portion of the lung including the identified area of interest by tracing the pulmonary artery through the lungs using EBUS scope 100. Once the particular vascular structure is identified, the location at which these structures are located are identified in the image data and stored in the memory coupled to computer 80 (FIG. 1). In this manner, the location of EBUS scope 100 within the luminal network of the lungs may be monitored utilizing sensor 108 and tracking system 70 (FIG. 1). EBUS scope 100 is removed from EWC 96 or the working channel of bronchoscope 50 and a suitable tool capable of cannulating the identified vascular structure is inserted within EWC 96 and navigated to the area of interest (FIG. 5). Cannulation can be performed using any suitable means; in one non-limiting embodiment, the identified vasculature is cannulated by means of a tool 200 capable of being inserted within bronchoscope 50 and/or EWC 96 having the ability to deploy venous and/or arterial cannulae 210 (FIG. 5). As can be appreciated, the tool 200 may be advanced within the bronchoscope 50 without the use of EWC 96 and navigated to the area of interest using a suitable sensor 208 (FIG. 5), as will be described in further detail hereinbelow.

By cannulating the identified vasculature, de-oxygenated/oxygenated blood traveling to and/or from the affected portion of the patient's lung is isolated by removing and reintroducing the blood before and after the affected portion of the pulmonary circulatory system. As noted above, although the alveoli are no longer perfused due to the bypass circuit that has been created by the cannulae, the isolated portion of the lung remains viable via bronchial circulation. As can be appreciated, a bypass circuit may be created utilizing the cannulae such that the blood may be isolated and recirculated within the isolated portion of the pulmonary circulatory system by means of an extracorporeal procedure such as extracorporeal membrane oxygenation. In certain embodiments, the bypass circuit described above, or alternatively, a small bypass circuit utilizing a perfusion device or other similar device known in the art, may recirculate diagnostics or therapeutics, such as drugs, isotope, or other modalities within the isolated portion of the vasculature to more effectively treat the diseased portion of the lungs. The use of the small bypass circuit provides the added benefit of more easily removing the diagnostics or therapeutics from the blood stream once the procedure is complete, thereby avoiding excessive exposure.

As can be appreciated, a bypass circuit as detailed above may not be required. Rather, the identified vascular structure may be cannulated using the procedure detailed above, and thereafter, therapeutics may be directed injected within the cannulated vasculature to treat the diseased portion of the lungs.

In embodiments, it is contemplated that an extracorporeal procedure may not be required. Alternatively, the cannulae are configured to block the flow of blood into and/or out of the inflow/outflow tracts or selected vein and/or artery. In this manner, the clinician creates a shunt, thereby shunting blood from the isolated portion of the lung to other portions of the lung, taking advantage of the lungs unique capability to adapt to increasing amounts of blood flowing therethrough, as noted hereinabove.

In embodiments, once the inflow and/or outflow tracts of the pulmonary and/or bronchial circulatory systems are identified by the clinician, a clamp or plurality of clamps may be applied to each identified vessel to isolate the affected portion of the lung. As can be appreciated, the clamps may be applied by a laparoscopic or open approach or a bronchoscopic approach. It is contemplated that the clamps may be a mechanical clamp capable of temporarily or permanently sealing the identified vascular structures, thereby creating a shunt. In embodiments, a clip applier or other similar device may be employed to temporarily or permanently ligate the identified vessels. Examples of clip appliers suitable for ligating the selected vessels are marketed and sold by Medtronic as Endo Clip™, Lapro-Clip™ and Surgiclip™.

Alternatively, it is envisioned that an electrosurgical device may be employed to permanently seal the inflow and/or outflow tracts via electrosurgical energy, such as a vessel sealer or the like. Such electrosurgical devices may be Medtronic's Ligasure® or other similar electrosurgical vessel sealing devices. For temporary sealing, it is contemplated that the clinician may employ forceps or other similar devices capable of temporarily clamping the vessel through a laparoscopic or open approach.

It is further envisioned that the clinician may employ internal devices to temporarily or permanently seal off the identified vascular structure. In this manner, the clinician may navigate a suitable tool 200 (FIG. 5) through the venous or arterial network of the lungs using a catheter suitable for navigation therethrough. Such catheters may employ a video or image capturing device and display the video and/or images on the monitoring equipment 60 (FIG. 1). As can be appreciated, the clinician may employ an electromagnetic navigation catheter, such as superDimension's Edge™ and superDimension™ navigation catheters to navigate a catheter to the area of interest using the procedure described hereinabove. The clinician may then advance the tool 200 within the catheter and place a clamp or other suitable device capable of blocking the flow of blood within the selected vessel(s). In this manner, the clinician penetrates the airway wall to deploy the clamp on the identified vessel.

At this point, several advantageous procedures may be performed on the area of interest. In one embodiment, the clinician may introduce drugs to the isolated portion of the lungs to treat the area of interest. Due to the pulmonary circulatory system being isolated, it is possible to deliver exceedingly high concentrations of drugs, such as cytotoxic agents (i.e., chemotherapy, antibiotics, viral or gene vectors, sensitizing agents, etc.), while being able to limit systemic circulation. In this manner, an otherwise normal dose of drugs would have greater efficacy than otherwise possible. Alternatively, a clinician may deliver doses that are far greater than possible with other procedures since the delivered drug will be isolated to the portion of the pulmonary circulatory system that has been cannulated. It is also contemplated that these vessels could be identified, cannulated, and without the need for isolation, a diagnostic or therapeutic modality introduced. The catheter would then be withdrawn and vascular defect sealed.

As can be appreciated, the above described procedure may alternatively be performed on the bronchial circulatory system. In this manner, the clinician may cannulate the vein and artery of the bronchial circulatory system serving the portion of the lung including the area of interest. The blood may then be recirculated by means of an extracorporeal procedure, with high doses of drugs introduced therein, such that the dose is restricted to the isolated portion of the bronchial circulatory system.

In another embodiment, isolating the portion of the pulmonary circulatory system serving the affected portion of the lung reduces a large heat sink of energy applied during electrosurgical and ablation procedures. Specifically, blood circulating with the lungs creates a heat sink that dissipates significant amounts of energy applied during electrosurgical procedures. This heat sink created by the circulating blood requires the application of a greater amount of energy than would ordinarily be required, increasing the likelihood of damaging surrounding tissue. Therefore, by inhibiting the flow of blood in the area of interest via isolating the pulmonary and/or bronchial circulatory systems, as described above, the clinician may reduce the amount of energy that is required to be applied to achieve a desired result. The reduction in the amount of energy applied reduces the potential of damaging surrounding tissue, thereby focusing treatment on the area of interest. It is envisioned that any suitable electrosurgical or microwave ablation device may be utilized to treat, resect, or otherwise remove lung tissue, including electrosurgical pencils, forceps, RF and microwave ablation catheters, or the like. Examples of such devices are sold and marketed by Medtronic and may be introduced via an endoscopic, open, or laparoscopic approach.

It is contemplated that EBUS scope 100 and tool 200 may include a sensor 108, 208 (FIG. 5), respectively that, in conjunction with tracking system 70 (FIG. 1), may be employed to enable tracking of a distal end of EBUS scope 100 and tool 200 as the distal ends thereof are advanced through the patient's airways, as detailed above. Thus, with additional reference to FIG. 1, computer 80, monitoring equipment 60, and/or any other suitable display may be configured to display the three-dimensional model and selected pathway, both of which were generated during the planning phase (as detailed above), along with the current location of the sensor 108, 208 disposed in the distal end of EBUS scope 100 and tool 200, respectively, to facilitate navigation of the distal end of EBUS scope 100 and tool 200 to the area of interest and/or manipulation of the distal end of EBUS scope 100 and tool 200 relative to the area of interest As can be appreciated, given the possibility of temporarily blocking or diverting flow of blood within the vascular structures, a database of the clinical consequences of such isolation and subsequent treatment can be built. In this manner, a clinician may monitor the patient's progress and responsiveness to the type of treatment and the amount of treatment administered. Specifically, the location of the area of interest is recorded in the memory coupled to the computer 80 (FIG. 1). The location at which the pulmonary and/or bronchial circulatory system is isolated is similarly recorded. The clinician further records whether the pulmonary and/or bronchial circulatory systems were cannulated, clamped, etc. and whether an extracorporeal procedure was performed. Additionally, the concentration of drugs administered to the area of interest is recorded. In this manner, the clinician monitors the progress of the treatment to determine if the concentration should be increased, decreased, or remain the same. It is contemplated that all of the above noted data is indexed to each specific patient, such that a clinician may easily identify similarly situated patients for future procedures. In this manner, recording of the effectiveness of the dose of drugs permits future clinicians treating similarly situated patient's to more effectively determine the correct treatment course and dosage. Thus, the treatment becomes more efficient by reducing the amount of drugs required, and/or the amount of procedures required, and therefore, reduces patient trauma and recovery time.

Similarly, it is contemplated that the clinician observe and monitor the patient to determine the clinical consequences of isolating the portion of the pulmonary and/or bronchial circulatory system serving the portion of the lung including the target tissue. In this manner, the clinician may monitor the patient's heart rate, respiration rate, oxygen saturation, breathing effort, or other vital signs indicative of whether the procedure has improved the patient's condition, maintained the patient's condition, or degraded the patient's condition. The clinician may then determine whether isolating the portion of the pulmonary and/or bronchial circulatory system produced the desired clinical effect. In this manner, if the temporary isolation produces the desired clinical effect, the clinician may remove or permanently isolate the portion of the lung that underwent temporary isolation. As can be appreciated, if the temporary isolation of the particular portion of the pulmonary and/or bronchial circulatory system resulted in deleterious effects, the clinician has identified that the planned procedure should not be undertaken. The clinical effects of the procedure are recorded in the database stored in the memory of the computer 80. In this manner, the location of the portion of the pulmonary circulatory system that was isolated is recorded in the memory and correlated to the location of the area of interest and the clinical record of the patient.

By recording the above described information, the clinical consequences of the procedure are made accessible by clinicians performing similar procedures in the future, and may be used to predict the clinical effect of similar procedures in the future. As can be appreciated, once the database is populated with a number of procedures and/or patients, a clinician will be able to predict or otherwise determine whether the planned procedure would produce the desired clinical effects. For example, a patient suffering from emphysema affecting a portion of the lungs located in the upper portion of the right lobe may be correlated to a similar patient having emphysema affecting a portion of the lungs located in the upper portion of the right lobe whose data has been entered into the database. In this manner, the clinician is able to predict whether removing or isolating this particular portion of the lung would produce the desired clinical effects. Indeed, by predicting whether a patient would benefit from removal or isolation of a particular portion of the lung, the clinician is able to reduce the number of procedures required to treat the patient (i.e., eliminating or vastly reducing a trial and error approach), thereby reducing pain, recovery time, and expense. Further, this predictive model provides a basis to determine whether a patient's outcome meets the prediction or falls short and if it falls short the clinician may be able to identify one or more aggravating factors not previously contemplated and perform further procedures. The data of these procedures is recorded and used to further the database for future clinicians.

Another embodiment of a procedure for isolating a portion of portion of a patient's pulmonary and/or bronchial circulatory system utilizes a predictive approach. Similarly as detailed above, this procedure is utilized in conjunction with tracking system 70 (FIG. 1) to facilitate navigation of EBUS scope 100 and tool 200 to a location adjacent the area of interest and or tracking of tool 200 as it is manipulated to isolate the portion of the pulmonary and/or bronchial circulatory system.

Once the area of interest is identified, the patient is compared to information stored in the database pertaining to other patients using a suitable software application executed by the processor. The process of identifying the area of interest is similar to that described above, and thus, will not be detailed herein for purposes of brevity. The software application compares the current patient's characteristics and the location of the area of interest to the entries populating the database, and using a mathematical computation or other similar means, identifies a particular patient or set of patients to which the current patient substantially aligns. As can be appreciated, the software application may assign a percentage or other identifier (e.g., ranking, number of similar characteristics, or the like) to patients stored within the database, such that the current patient may be considered a 100% match, 95% match, or the like. It is further contemplated that the software application may rank or otherwise compile, in descending or ascending order, a list of identified patients. Using this information, the clinician may make an educated determination as to the likelihood that removing or isolating that particular portion of the vascular structure would produce the desired clinical effect. With this information available to the clinician during the planning phase, the clinician may make an informed decision to either temporarily isolate the portion of the vascular structure serving the area of interest, as described hereinabove, or permanently isolate and/or remove the tissue or vascular structure containing or serving the area of interest.

Finally, using the software application described above, the clinician observes the clinical effects similarly to that described above, and thereafter, records the clinical effects of the procedure and enters the information into the database. In embodiments, it is envisioned that the clinician records the clinical effects regardless of whether he chose to permanently isolate or merely temporarily isolate the vascular structure serving the portion of the lungs including the area of interest. This ensures that the database is continually updated such that further clinicians receive the most up to date and reliable information possible when planning future procedures.

Yet a further aspect of the present disclosure is a predictive outcome application. With all the procedures described herein, there will be follow-up CT imaging and most likely pulmonary function testing. These data, particularly the CT image data and particularly contrast enhanced CT imaging or PET/CT imaging, can be collected in an effort to identify the actual outcomes associated with the treatments described herein and at a minimum determine if follow-up procedures are necessary. By comparing actual outcomes to the treatment parameters better guidelines can be given to the clinicians. More importantly the planning software (described above) can rely on this data to adjust the expected treatment zone given a wide array of factors including size of alveolus or lung parencyma treated, size of blood vessels in the treatment area, location in the lung (e.g., which bifurcation), power and duration of ablation and others. As a result, over time the predictions in the planning software are refined to provide greater accuracy. It is also anticipated that the above described software could alert surgeons and proceduralists to aberrant distributions of the vasculature that would be valuable to know pre-procedurally. In this manner, the identified aberrant distributions could be used to alter operative or procedural planning.

Referring again to FIG. 1, patient "P" is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50 and/or ultrasound image obtained by the EBUS scope 100. In embodiments, it is contemplated that bronchoscope 50 may be any suitable bronchoscope capable of navigating the airways of a patient and permitting an EBUS scope 100 or other suitable tool to be inserted therein (such as tool 200 detailed hereinabove). For a detailed description of an exemplary bronchoscope 50, reference can be made to U.S. Patent Application Publication No. 2015/0265257 to Costello et al. entitled "Systems, and Methods for Navigating a Biopsy Tool to a Target Location and Obtaining a Tissue Sample Using the Same", filed Dec. 9, 2014, the entire contents of which are incorporated by reference herein.

System 10 includes a navigation system capable of guiding bronchoscope 50 to an area of interest. The navigation system may be a six degrees-of-freedom electromagnetic tracking system 70, e.g., similar to those disclosed in U.S. patent application Ser. No. 14/753,288 to Brown et al. entitled "System and Method for Navigating within the Lung", filed Jun. 29, 2015 and published PCT Application Nos. WO 00/10456 and WO 01/67035, the entire contents of each of which is incorporated herein by reference, or other suitable positioning measuring system, is utilized for performing registration and navigation, although other configurations are also contemplated. Tracking system 70 includes a tracking module 72, a plurality of reference sensors 74, and a transmitter mat 76. Tracking system 70 is configured for use with either positioning assembly 90 or positioning assembly 91, EBUS scope 100 (FIGS. 2A and 2B), and tool 200 (FIG. 5), as detailed below. Positioning assemblies 90 and 91 further include EWC 96 and a handle 120. LG 92 and EWC 96 are configured for insertion through a working channel of bronchoscope 50 into the patient's airways (although LG 92 and EWC 96 may alternatively be used without bronchoscope 50) and are selectively lockable relative to one another via a locking mechanism 99. Distal tip 93 of LG 92 may be configured for steering in any suitable fashion, e.g., using a plurality of steering wires (not shown) coupled between handle 98 and distal tip 93, to facilitate maneuvering distal tip 93 of LG 92 and EWC 96 through the patient's airways. Alternatively, rotation and translation of handle 120 may facilitate maneuvering of the distal tip 93 of LG 92, and in particular embodiments the EWC 96 may be angled or curved to assist in maneuvering the distal tip 93 through the airways. Sensor 94 is integrated with distal tip 93 of LG 92 and allows monitoring of the position and orientation of distal tip 93, in six degrees of freedom, relative to the reference coordinate system. For a detailed description of the construction of exemplary navigation systems, reference may be made to U.S. Patent Application Publication No. 2015/0265257 to Costello et al., previously incorporated by reference.

A transmitter mat 76 is positioned beneath the patient "P" and is a transmitter of electromagnetic radiation. Transmitter mat 76 includes a stack of three substantially planar rectangular loop antennas (not shown) configured to be connected to drive circuitry (not shown). For a detailed description of the construction of exemplary transmitter mats, which may also be referred to as location boards, reference may be made to U.S. Patent Application Publication No. 2009/0284255 to Zur entitled "Magnetic Interference Detection System and Method", filed Apr. 2, 2009, the entire contents of which are incorporated by reference herein.

Transmitter mat 76 and the plurality of reference sensors 74 are interconnected with tracking module 72, which derives the location of each sensor 74 in six degrees of freedom. One or more of reference sensors 74 are attached to the chest of the patient "P." The six degrees of freedom coordinates of reference sensors 74 are sent to computer 80 (which includes the appropriate software) where they are used to calculate a patient coordinate frame of reference. Registration, as detailed below, is generally performed by identifying locations in both the three-dimensional model and the patient's airways and measuring the coordinates in both systems. Further details of such a registration technique can be found in U.S. Patent Application Pub. No. 2011/0085720 to Barak et al. entitled "Automatic Registration Technique", filed May 14, 2010, the entire contents of which are incorporated herein by reference, although other suitable registration techniques are also contemplated.

In use, with respect to the navigation phase, LG 92 is inserted into positioning assembly 90, 91, and EWC 96 such that sensor 94 projects from the distal end of EWC 96. LG 92 and EWC 96 are then locked together via locking mechanism 99 (for example). LG 92, together with EWC 96, are then inserted through bronchoscope 50 and into the airways of the patient "P," with LG 92 and EWC 96 moving in concert with one another through bronchoscope 50 and into the airways of the patient "P." Automatic registration is performed by moving LG 92 through the airways of the patient "P." More specifically, data pertaining to locations of sensor 94 while LG 92 is moving through the airways is recorded using transmitter mat 76, reference sensors 74, and tracking module 72. A shape resulting from this location data is compared to an interior geometry of passages of the three-dimensional model generated in the planning phase, and a location correlation between the shape and the three-dimensional model based on the comparison is determined, e.g., utilizing the software on computer 80. In addition, the software identifies non-tissue space (e.g., air filled cavities) in the three-dimensional model. The software aligns, or registers, an image representing a location of sensor 94 of LG 92 with an image of the three-dimensional model based on the recorded location data and an assumption that LG 92 remains located in non-tissue space in the patient's airways. This completes the registration portion of the navigation phase.

Referring still to FIG. 1, once the planning phase has been completed, e.g., the target tissue has been identified and the pathway thereto selected, and registration has been completed, system 10 may be utilized to navigate LG 92 through the patient's airway to the area of interest. To facilitate such navigation, computer 80, monitoring equipment 60, and/or any other suitable display may be configured to display the three-dimensional model including the selected pathway from the current location of sensor 94 of LG 92 to the area of interest. Navigation of LG 92 to the area of interest using tracking system 70 is similar to that detailed above and thus, is not detailed here for the purposes of brevity.

Once LG 92 has been successfully navigated to the area of interest, completing the navigation phase, LG 92 may be unlocked from EWC 96 and removed, leaving EWC 96 in place as a guide channel for guiding EBUS scope 100 and/or tool 200. For a detailed description of exemplary navigation and planning phases, reference may be made to U.S. patent application Ser. No. 14/753,288 to Brown et al., previously incorporated by reference.

The electromagnetic waves generated by transmitter mat 76 are received by the various sensor elements configured for use with EBUS scope 100 and tool 200 or sensor 94 of LG 92, and are converted into electrical signals that are sensed via reference sensors 74. Tracking system 70 further includes reception circuitry (not shown) that has appropriate amplifiers and A/D converters that are utilized to receive the electrical signals from reference sensors 74 and process these signals to determine and record location data of the sensor assembly. Computer 80 may be configured to receive the location data from tracking system 70 and display the current location of the sensor assembly on the three-dimensional model and relative to the selected pathway generated during the planning phase, e.g., on computer 80, monitoring equipment 60, or other suitable display. Thus, navigation of EBUS scope 100, tool 200, and/or LG 92 to the target tissue and/or manipulation of tool 200 relative to the target tissue, as detailed above, can be readily achieved.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

As used hereinabove, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. Additionally, in the drawings and in the description above, terms such as front, rear, upper, lower, top, bottom, and similar directional terms are used simply for convenience of description and are not intended to limit the disclosure. In the description hereinabove, well-known functions or constructions are not described in detail to avoid obscuring the present disclosure in unnecessary detail.

What is claimed is:

1. A method of performing a surgical procedure, comprising:
   receiving image data of a patient's lungs;
   identifying an area of interest within the received image data;
   determining a direction of blood flow within a vascular structure within the patient's lungs serving the area of interest via a tool positioned at the area of interest;
   monitoring a clinical effect of temporarily obstructing the flow of blood within the vascular structure and isolating a portion of the patient's circulatory system serving the lungs; and comparing the monitored clinical effect to a predicted clinical effect of temporarily obstructing the flow of blood within the vascular structure and isolating a portion of the patient's circulatory system serving the lungs.

2. The method of claim 1, wherein the tool is positioned at the area of interest using ultrasound images obtained by an endobronchial ultrasound scope.

3. The method of claim 2, wherein determining the direction of blood flow within the vascular structure includes processing doppler signals received from the endobronchial ultrasound scope to identify the direction of blood flow within the vascular structure.

4. The method of claim 1, further including:
monitoring the clinical effect of temporarily obstructing the flow of blood within the vascular structure using a second tool to cannulate the vascular structure.

5. The method of claim 1, further including monitoring an effect of extracorporeal circulation of blood from the vascular structure.

6. The method of claim 5, wherein monitoring an effect of extracorporeal circulation of blood includes receiving a drug within the isolated portion of the circulatory system.

7. The method of claim 1, wherein monitoring the clinical effect of temporarily obstructing the flow of blood within the vascular structure includes monitoring the clinical effect of temporarily obstructing the flow of blood within the patient's pulmonary circulatory system serving adjacent the area of interest.

8. The method of claim 1, wherein monitoring a clinical effect of temporarily obstructing the flow of blood within the vascular structure includes monitoring the clinical effect of temporarily obstructing the flow of blood within the patient's bronchial circulatory system serving the area of interest.

9. A method of performing a surgical procedure, comprising:
storing software on a memory associated with a computer, which when executed causes a processor to:
acquire an image of a patient's lungs;
identify an area of interest on the acquired image;
identify a similar patient from a database stored within the memory; and
predict a clinical effect of isolating a portion of the circulatory system within the patient's lungs serving the area of interest; and
monitoring a clinical effect of isolating the portion of the circulatory system within the patient's lungs serving the area of interest.

10. The method of claim 9, wherein predicting the clinical effect of isolating the portion of the circulatory system includes predicting a dose of drugs to be received by the isolated portion of the circulatory system.

11. The method of claim 10, further including receiving a predicted dose of drugs within the isolated portion of the circulatory system.

12. The method of claim 9, further including comparing the monitored clinical effect with the predicted clinical effect of isolating the portion of the circulatory system within the patient's lungs serving the area of interest.

13. A method of performing a surgical procedure, comprising:
determining a direction of blood flow within vascular structure within a patient's lungs serving an area of interest via a tool positioned at the area of interest;
predicting a clinical effect of temporarily obstructing the flow of blood within the vascular structure and isolating a portion of the patient's circulatory system serving the area of interest; and
monitoring the clinical effect of temporarily obstructing the flow of blood within the vascular structure and isolating the portion of the patient's circulatory system serving the area of interest.

14. The method of claim 13, further comprising comparing the monitored clinical effect to a predicted clinical effect of temporarily obstructing the flow of blood within the vascular structure and isolating the portion of the patient's circulatory system serving the area of interest.

15. The method of claim 13, wherein the tool is positioned at the area of interest using ultrasound images obtained by an endobronchial ultrasound scope.

16. The method of claim 15, wherein determining the direction of blood flow within the vascular structure includes processing doppler signals received from the endobronchial ultrasound scope to identify the direction of blood flow within the vascular structure.

17. The method of claim 13, further including monitoring an effect of extracorporeal circulation of blood from the vascular structure.

18. The method of claim 17, wherein monitoring an effect of extracorporeal circulation of blood includes receiving a drug within the isolated portion of the patient's circulatory system.

19. The method of claim 13, wherein monitoring the clinical effect of temporarily obstructing the flow of blood within the vascular structure includes monitoring the clinical effect of temporarily obstructing the flow of blood within the patient's pulmonary circulatory system serving adjacent the area of interest.

20. The method of claim 13, wherein monitoring the clinical effect of temporarily obstructing the flow of blood within the vascular structure includes monitoring the clinical effect of temporarily obstructing the flow of blood within the patient's bronchial circulatory system serving the area of interest.

* * * * *